(12) United States Patent
Barenboym et al.

(10) Patent No.: US 8,992,470 B2
(45) Date of Patent: Mar. 31, 2015

(54) CONTROL MECHANISM FOR STEERABLE MEDICAL DEVICE

(75) Inventors: Michael Barenboym, Framingham, MA (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 961 days.

(21) Appl. No.: 11/804,422

(22) Filed: May 18, 2007

(65) Prior Publication Data

US 2007/0282167 A1 Dec. 6, 2007

Related U.S. Application Data

(60) Provisional application No. 60/801,808, filed on May 19, 2006.

(51) Int. Cl.
| | | |
|---|---|---|
| A61M 31/00 | (2006.01) | |
| A61M 37/00 | (2006.01) | |
| A61B 1/005 | (2006.01) | |
| A61M 25/01 | (2006.01) | |

(52) U.S. Cl.
CPC .......... *A61B 1/0052* (2013.01); *A61M 25/0136* (2013.01); *A61B 1/0053* (2013.01)
USPC ....................................... 604/95.04; 600/131

(58) Field of Classification Search
USPC ............ 604/95.01, 95.04, 523, 528; 600/433, 600/434, 435, 585, 131; 607/125
See application file for complete search history.

(56) References Cited

U.S. PATENT DOCUMENTS

| | | | |
|---|---|---|---|
| 4,566,437 A | 1/1986 | Yamaguchi | |
| 4,617,915 A | 10/1986 | Arakawa | |
| 4,998,916 A | 3/1991 | Hammerslag et al. | |
| 5,060,660 A | 10/1991 | Gambale et al. | |
| 5,281,214 A | 1/1994 | Wilkins et al. | |
| 5,325,845 A | 7/1994 | Adair | |
| 5,347,989 A | 9/1994 | Monroe et al. | |
| D351,652 S | 10/1994 | Thompson et al. | |
| 5,352,237 A | 10/1994 | Rodak et al. | |
| 5,413,107 A * | 5/1995 | Oakley et al. | ................. 600/463 |
| 5,462,527 A | 10/1995 | Stevens-Wright et al. | |
| 5,611,777 A | 3/1997 | Bowden et al. | |
| 5,656,030 A | 8/1997 | Hunjan et al. | |
| 5,667,476 A | 9/1997 | Frassica et al. | |
| 5,702,349 A | 12/1997 | Morizumi | |
| 5,860,953 A | 1/1999 | Snoke et al. | |

(Continued)

FOREIGN PATENT DOCUMENTS

| | | |
|---|---|---|
| EP | 0 521 595 B1 | 5/1999 |
| EP | 0 668 052 B1 | 1/2003 |

(Continued)

OTHER PUBLICATIONS

Notification Concerning Transmittal of International Preliminary Report on Patentability mailed Dec. 4, 2008, issued in corresponding international application No. PCT/US2007/011912.

(Continued)

*Primary Examiner* — Theodore Stigell
(74) *Attorney, Agent, or Firm* — Bookoff McAndrews, PLLC

(57) ABSTRACT

A control mechanism for use with a steerable medical device allows for single-handed operation of at least a distal portion of the medical device. The device can be a catheter or an endoscope, for example.

26 Claims, 11 Drawing Sheets

(56) References Cited

U.S. PATENT DOCUMENTS

| | | | |
|---|---|---|---|
| 5,882,333 | A | 3/1999 | Schaer et al. |
| 5,897,529 | A | 4/1999 | Ponzi |
| 5,906,590 | A | 5/1999 | Hunjan et al. |
| 5,957,865 | A | 9/1999 | Backman et al. |
| 6,007,531 | A | 12/1999 | Snoke et al. |
| 6,027,473 | A | 2/2000 | Ponzi |
| 6,059,739 | A | 5/2000 | Baumann |
| 6,066,125 | A | 5/2000 | Webster, Jr. |
| 6,123,699 | A | 9/2000 | Webster, Jr. |
| 6,171,277 | B1 | 1/2001 | Ponzi |
| 6,183,435 | B1 | 2/2001 | Bumbalough et al. |
| 6,183,463 | B1 | 2/2001 | Webster, Jr. |
| 6,198,974 | B1 | 3/2001 | Webster, Jr. |
| 6,203,507 | B1 | 3/2001 | Wadsworth et al. |
| 6,267,746 | B1 | 7/2001 | Bumbalough |
| 6,361,219 | B1 | 3/2002 | Blyler, Jr. et al. |
| 6,468,260 | B1 | 10/2002 | Bumbalough et al. |
| 6,500,167 | B1 | 12/2002 | Webster, Jr. |
| 6,571,131 | B1 | 5/2003 | Nguyen |
| 6,605,086 | B2 | 8/2003 | Hayzelden et al. |
| 6,679,873 | B2 | 1/2004 | Rabiner et al. |
| 6,783,510 | B1 | 8/2004 | Gibston et al. |
| 6,802,835 | B2 | 10/2004 | Rabiner et al. |
| 6,837,867 | B2 | 1/2005 | Kortelling |
| 6,855,137 | B2 | 2/2005 | Bon |
| 6,916,306 | B1* | 7/2005 | Jenkins et al. ............. 604/95.04 |
| 6,945,956 | B2 | 9/2005 | Waldhauser et al. |
| 6,966,906 | B2 | 11/2005 | Brown |
| 7,022,102 | B2* | 4/2006 | Paskar ....................... 604/95.04 |
| 7,037,290 | B2 | 5/2006 | Gardeski et al. |
| 7,060,024 | B2 | 6/2006 | Long et al. |
| 7,060,025 | B2 | 6/2006 | Long et al. |
| 7,060,052 | B2 | 6/2006 | Windheuser et al. |
| 7,076,285 | B2 | 7/2006 | Windheuser et al. |
| 7,115,134 | B2 | 10/2006 | Chambers |
| 7,232,437 | B2 | 6/2007 | Berman et al. |
| 7,238,180 | B2 | 7/2007 | Mester et al. |
| 7,276,062 | B2 | 10/2007 | McDaniel et al. |
| 2002/0133077 | A1 | 9/2002 | Edwardsen et al. |
| 2004/0193239 | A1* | 9/2004 | Falwell et al. ................ 607/122 |
| 2005/0080476 | A1 | 4/2005 | Gunderson et al. |
| 2005/0256375 | A1 | 11/2005 | Freed |
| 2005/0277874 | A1 | 12/2005 | Selkee |
| 2005/0277875 | A1 | 12/2005 | Selkee |
| 2005/0288627 | A1* | 12/2005 | Mogul ....................... 604/95.04 |
| 2006/0142694 | A1 | 6/2006 | Bednarek et al. |
| 2006/0173448 | A1 | 8/2006 | Scheller et al. |
| 2006/0252993 | A1 | 11/2006 | Freed et al. |
| 2007/0156116 | A1 | 7/2007 | Gonzalez |
| 2007/0203474 | A1 | 8/2007 | Ryan et al. |
| 2007/0270647 | A1 | 11/2007 | Nahen et al. |
| 2008/0051802 | A1 | 2/2008 | Schostek et al. |
| 2009/0171275 | A1 | 7/2009 | Ostrovsky et al. |

FOREIGN PATENT DOCUMENTS

| | | |
|---|---|---|
| WO | WO 93/20878 A | 10/1993 |
| WO | WO 99/62585 A1 | 12/1999 |
| WO | WO 2007/136829 A1 | 11/2007 |

OTHER PUBLICATIONS

Notification of Transmittal of the International Search Report and the Written Opinion of the International Searching Authority, or the Declaration mailed Sep. 12, 2008, issued in corresponding international application No. PCT/US07/11912.

International Search Report and Written Opinion for PCT/US08/86142, mailed on Mar. 11, 2009; 10 pages.

International Search Report and Written Opinion for PCT/US09/34831, mailed on May 13, 2009; 13 pages.

International Search Report and Written Opinion for PCT/US09/48792, mailed on Sep. 22, 2009; 15 pages.

Extended European search report including the Supplementary European search report and the European search opinion, dated Jul. 22, 2010, issued in corresponding EP Application No. 07 809 098.2, 8 pages.

Extended European Search Report for corresponding EP Application No. 13157632.4 dated May 23, 2013 (7 pages).

* cited by examiner

US 8,992,470 B2

CONTROL MECHANISM FOR STEERABLE MEDICAL DEVICE

CROSS-REFERENCE TO RELATED APPLICATION

This claims priority to and the benefit of Provisional U.S. Patent Application Ser. No. 60/801,808, filed May 19, 2006, the entirety of which is incorporated herein by reference.

TECHNICAL FIELD

The invention generally relates to control mechanisms for medical devices such as steerable catheters or steerable endoscopes. More particularly, the invention generally relates to such mechanisms that enable an operator to control movement of a distal end or distal portion end of an elongated medical device in a plurality of planes with a single hand.

BACKGROUND INFORMATION

Known catheters and endoscopes for use in minimally invasive surgical procedures typically move only in one plane and are difficult to manipulate and control effectively with a single hand of an operator. Single plane movement generally requires a medical device, such as a catheter, that is flexible in a first plane and rigid in a second plane that is perpendicular to the first plane. Manufacturing such a device can be relatively expensive. U.S. Pat. No. 5,656,030 to Hunjan et al. describes a bidirectional steerable catheter that includes a handle, a deflectable tip, and a tubular member extending between the handle and the tip. Steering wires run through a tubular member and provide control of the tip.

BRIEF DESCRIPTION OF THE DRAWINGS

The accompanying drawings, which are incorporated in and constitute part of this specification, are included to illustrate and provide a further understanding of the disclosed methods and systems and technology. The drawings help to show principles of construction and operation. The drawings are illustrative, but not limiting.

DESCRIPTION

Figure 1:
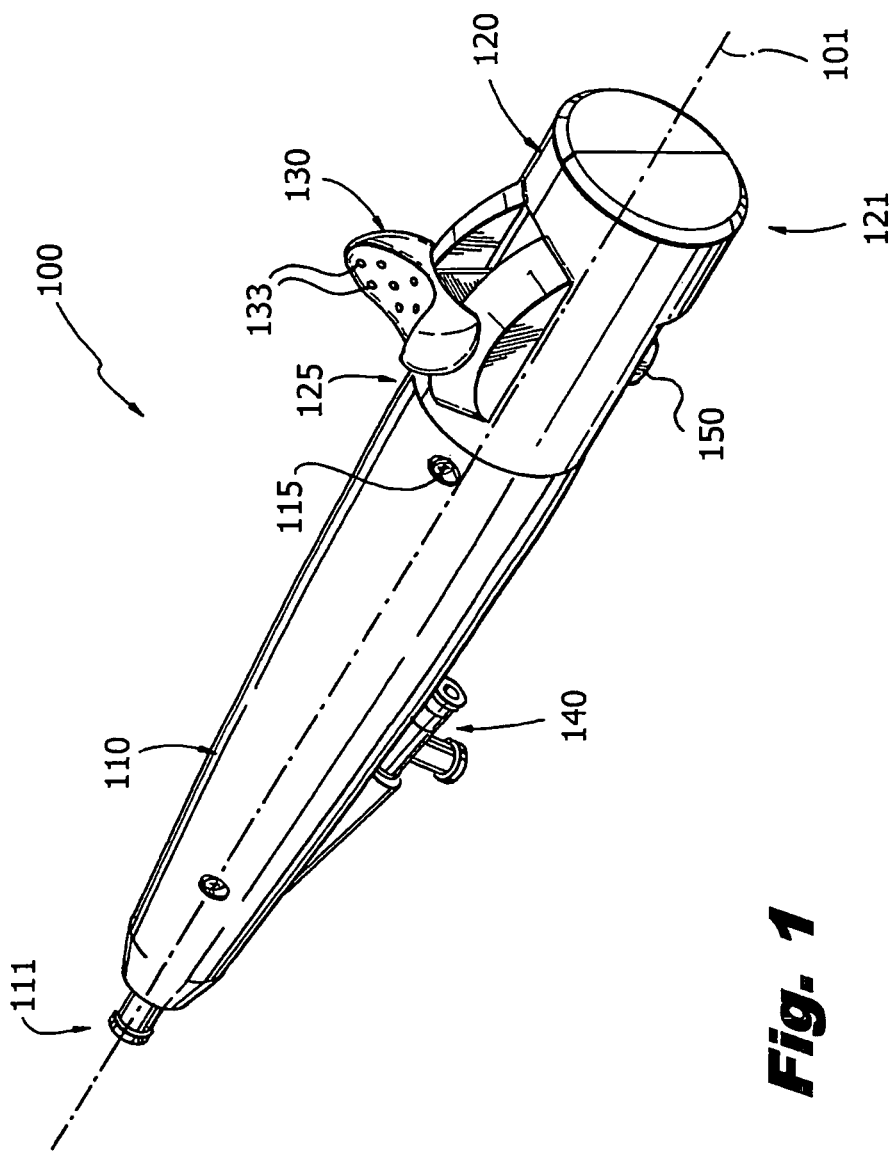
FIG. 1 is an isometric view of a first representative embodiment of a handle for a control mechanism for a steerable catheter or endoscope.
Figure 2:
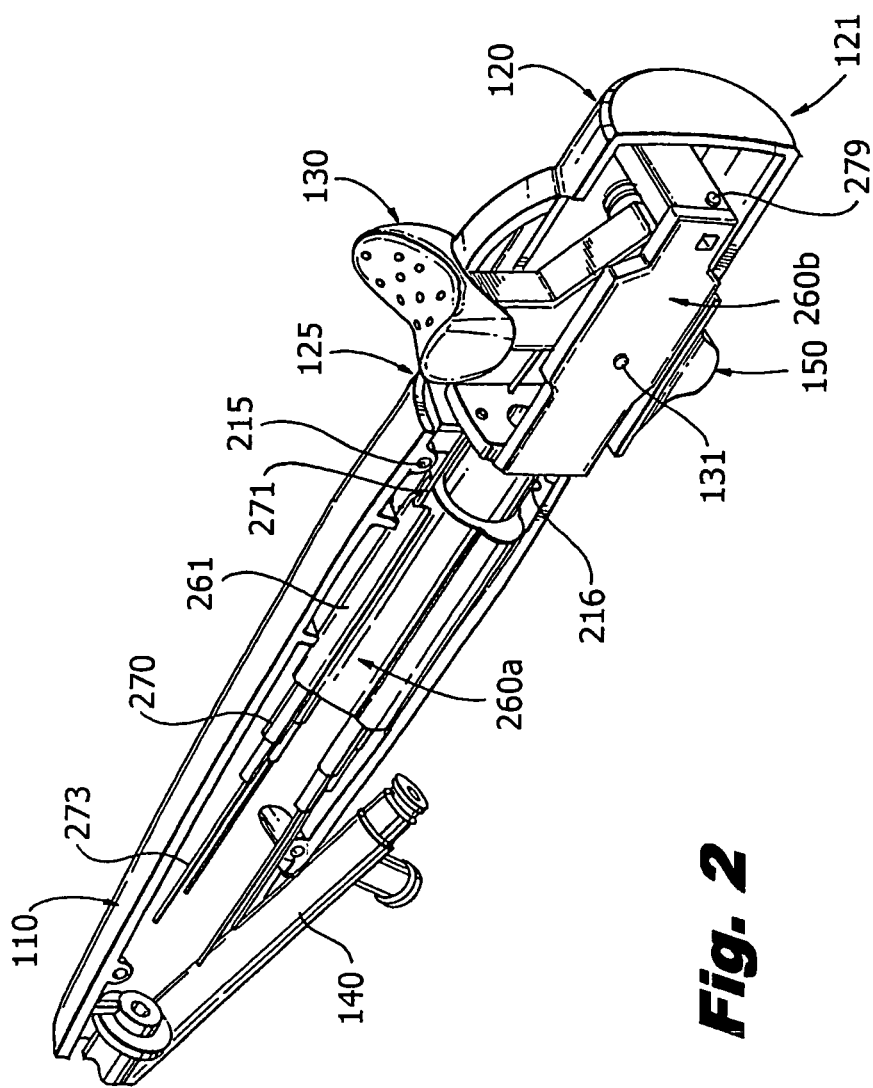
FIG. 2 is a cutaway view of the handle of FIG. 1.

The following description presents details of embodiments and examples according to the invention, but the description is not intended to be limiting on the invention. The devices and methods presented herein may be used for manipulating a relatively thin and flexible elongate device. These devices and methods are particularly suited for manipulating the elongate shaft, or just a distal portion of such a shaft, of an endoscope or catheter during surgical procedures such as minimally invasive procedures.

For purpose of explanation and illustration, and not limitation, various views of an exemplary embodiment of a handle, housing a control mechanism, is shown in FIGS. 1-10 and is designated generally by reference character 100. Another embodiment of a handle 1100 with a control mechanism is provided in FIG. 11, as will be described.

The handle 100 includes a main handle portion 110 and a rotatable handle portion 120, each of which is aligned along a common longitudinal axis 101. Reference number 111 indicates a distal end of the handle, with a proximal end indicated by reference number 121.

Figure 4:
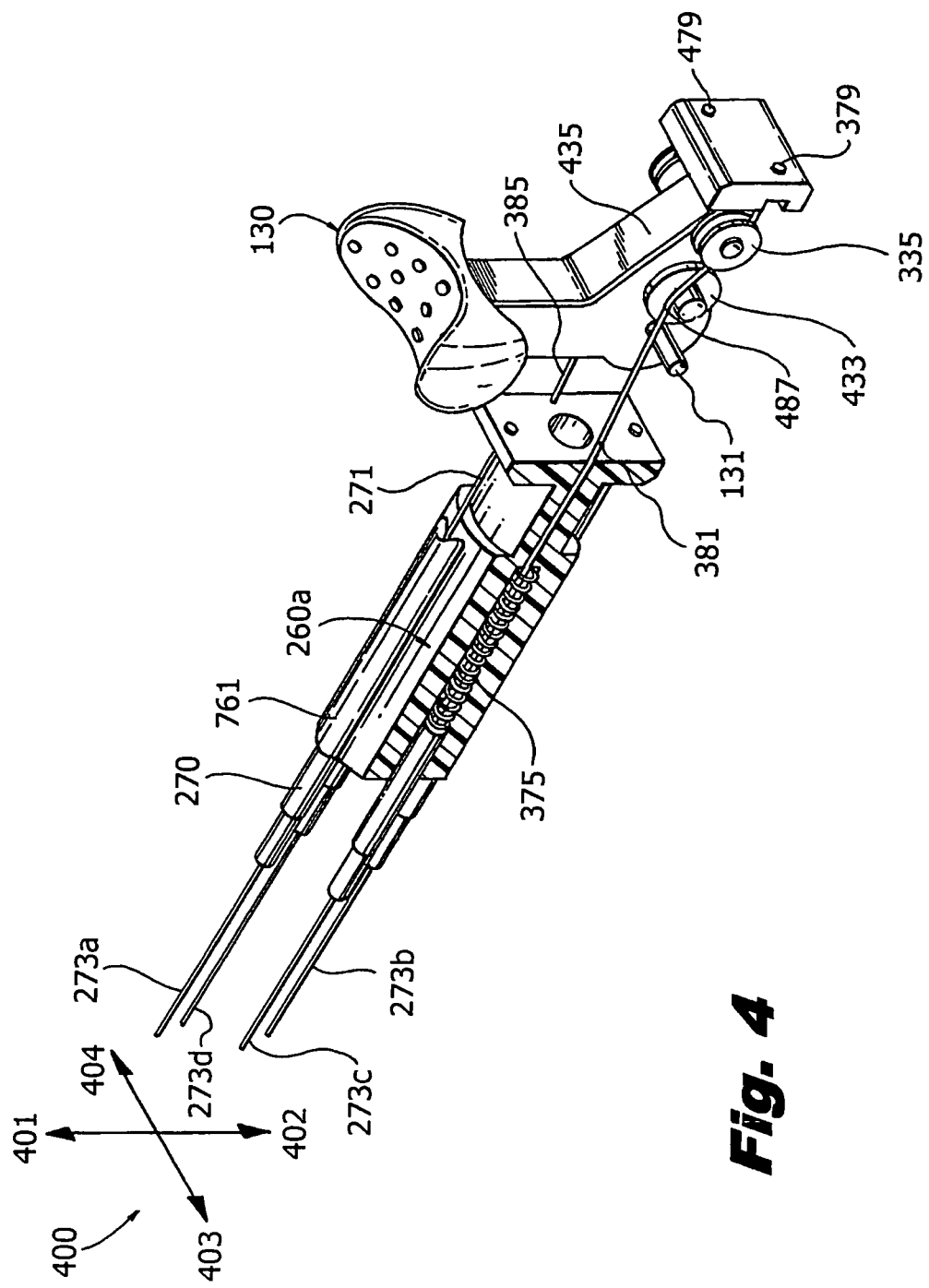
FIG. 4 is a left isometric exploded view of the handle of FIG. 1, illustrating only internal components of the handle.

FIG. 4 includes, for illustrative purposes, a coordinate axis 400, illustrating up 401, down 402, left 403 and right 404 directions, as will be referred to herein. Also as seen in FIG. 4, four control wires 273a-d are provided, which correspond to each of these four directions, each is configured at about 90 degrees from each adjacent control wire with respect to the longitudinal axis 101. This arrangement of control wires, each of which is controllable by an operator, enables convenient control of a catheter or endoscope in any direction, that is in 360-degrees, about the longitudinal axis 101. While four cables are illustrated, the principles of the invention can readily be applied to devices having one, two, three, four, five, six or more control wires, as needed or desired. Such control wires can be arranged at regular angular intervals around the longitudinal axis 101.

A thumb-control lever 130 is provided in the rotatable handle portion 120, and has a relatively deep concave contour and gripping elements 133 to facilitate secure control with a user's thumb. This lever 130 rotates along the longitudinal axis 101 with the rotatable handle portion 120. The lever 130 also pivots on pin 131, with respect to an inner mechanism frame 260b. See FIG. 2, for example.

This mechanism frame 260b is rigidly attached to or integrally formed with a turret 260a, which guides control wires and/or cables and can house return springs 375 in lobular portions 261. The frame 260b and turret 260a rotate along the longitudinal axis 101 with the rotatable handle portion 120, relative to the main handle portion 110. A lock 150 is provided to lock the position of the lever 120 and the rotatable handle portion 120, when desired.

Control wires 273a-d, which extend through the catheter/endoscope shaft 990 (FIG. 9) impart control movements to the end of the catheter/endoscope, and terminate at couplings 270. Control cables 271 are secured to the couplings and run toward the proximal end 121 of the handle 100, but terminate at predetermined locations.

Figure 3:
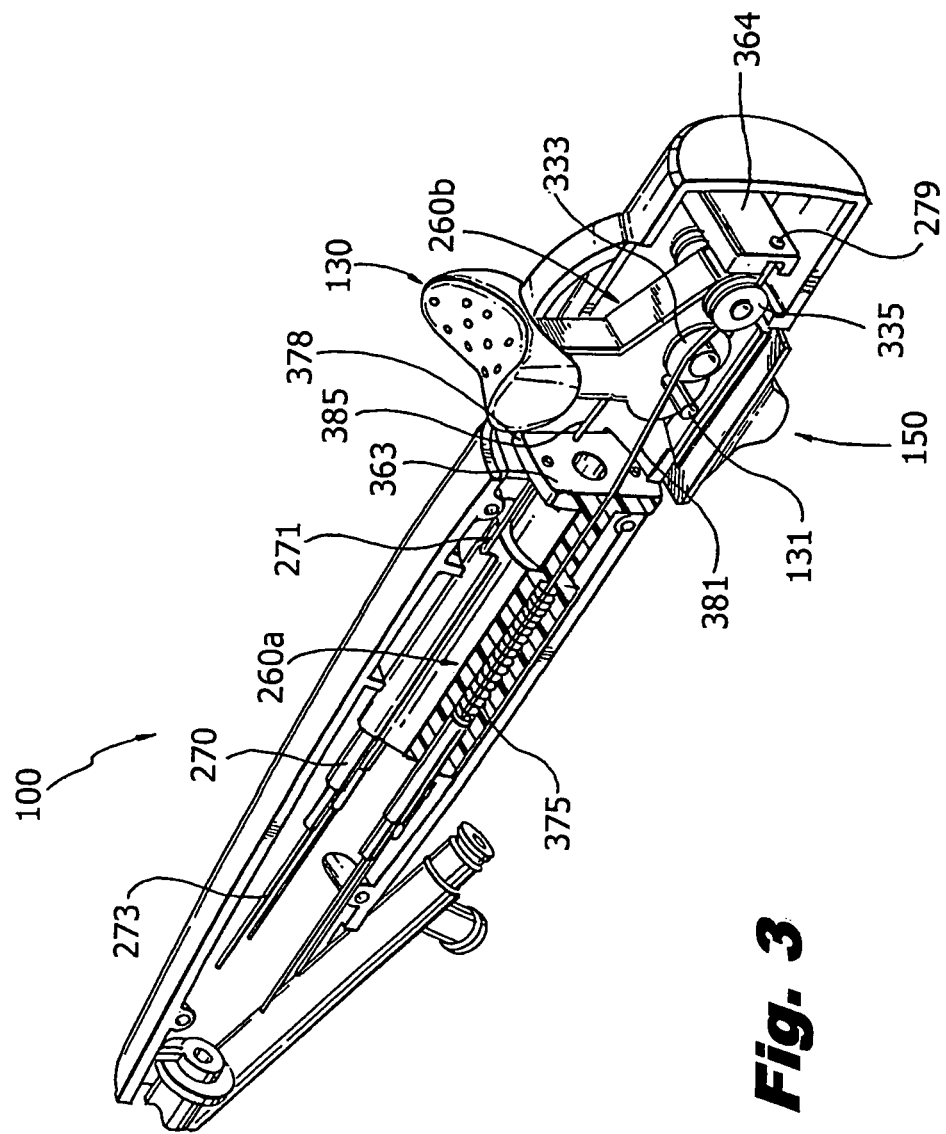
FIG. 3 is a further cutaway view of the handle of FIG. 1.

As can be seen in FIG. 3, upper control cable 271 terminates at a termination 378 in distal end wall 363 of the frame 260b. A lower control cable 572 (FIG. 5) terminates in a similar fashion in the end wall 363. Side control cables 381, 385 terminate in a proximal end wall 364 at terminations 279.

As seen in FIGS. 3-5 and 10, the side control cable 381 passes through the turret portion 260a, and between two rollers 333, 335, while control cable 385 passes through the turret portion 260a and between rollers 537, 539 on the opposite side of the lever 130.

The springs (e.g. springs 375, 577) are situated within the turret 260a such that when tension is applied to the control cables 381, 385, 271 or 572, the respective coupling element 270 is urged toward the proximal end 121 of the handle 100, thereby compressing the respective spring. It is contemplated that the device can alternatively be provided without such return springs, or that certain control aspects can be provided with return springs, and other control aspects not provided with such springs. This determination can be made on the bases of the task at hand and user preference.

While coupling elements 270 enable containment and compression of return springs (e.g., springs 375, 577), as illustrated, they also facilitate use of different materials for control wires 273a-d, which extend through the endoscope/catheter shaft 990 (FIG. 9), and for control cables (e.g., cable 381) in the handle. This provides an advantage that relatively stiff materials can be used for the control wires 273, while relatively flexible materials can be used for the control cables. For example, even a woven material can be used as a control cable. Since the movement of the control elements, such as the lever 130 and the moveable handle portion 120, can be extreme enough so as to plastically deform certain rigid materials, this decoupling of the control lines may be desirable.

As seen in FIGS. 2, 3, 8 and 9, a port 140 is provided for insertion of any necessary instrumentation during a procedure. Screws 115 are provided to assemble the handle 100, although the handle can be assembled by way of a snap fit, adhesive, weld, or other suitable connection.

In use, an operator, such as a surgeon, will hold the main handle portion 110 in one hand to support the handle 100, to allow the operator to insert the catheter or endoscope into the patient, adjusting the longitudinal position of the catheter or endoscope. The operator positions his/her other hand on the rotatable handle portion 120, placing his/her thumb on lever 130. Directions will be described with respect to the orientation of the handle 100 illustrated in the figures, although this orientation would likely be different in actual use, bearing in mind that the precise configuration of the device mechanism can easily be reconfigured depending on the desired nature and behavior of the controls.

Figure 5:
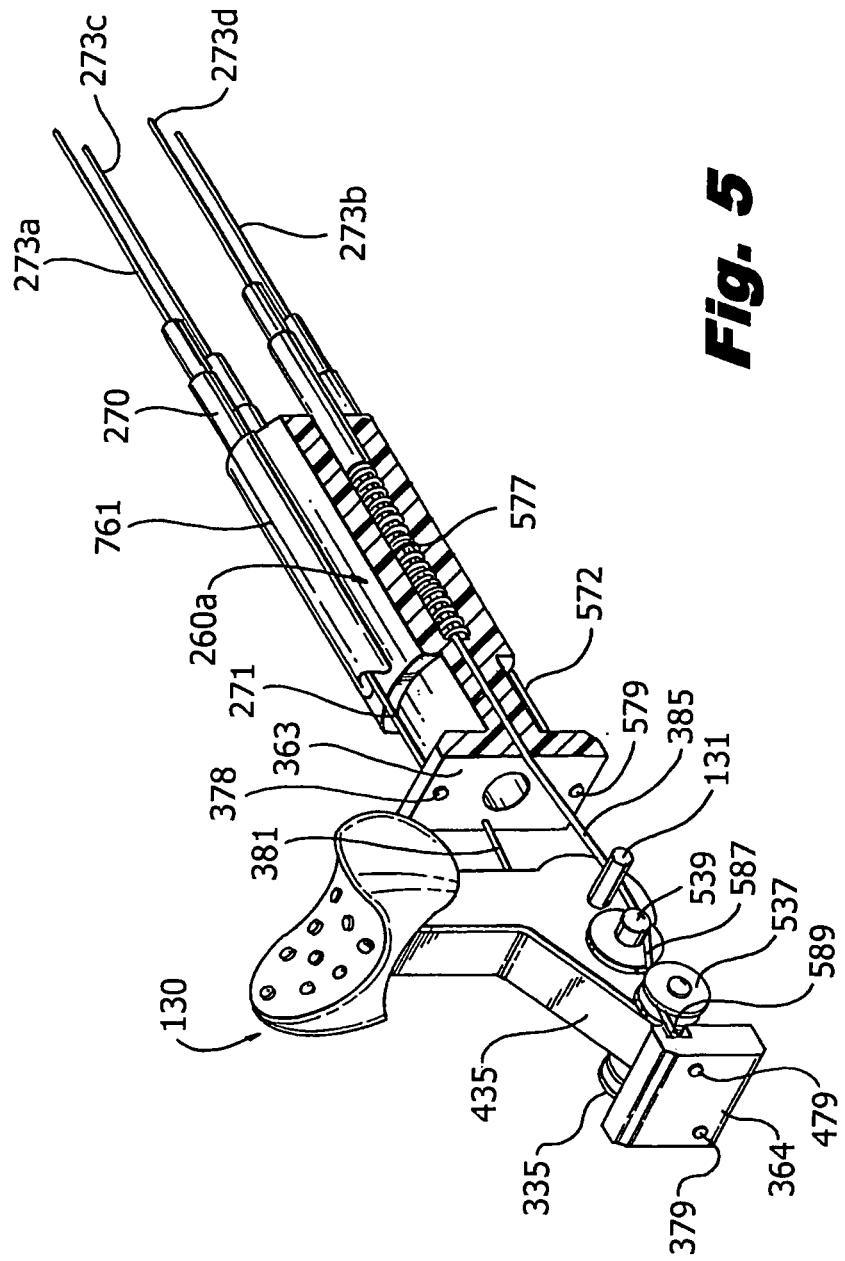
FIG. 5 is a right isometric exploded view of the handle of FIG. 1, illustrating only internal components of the handle.
Figure 6:
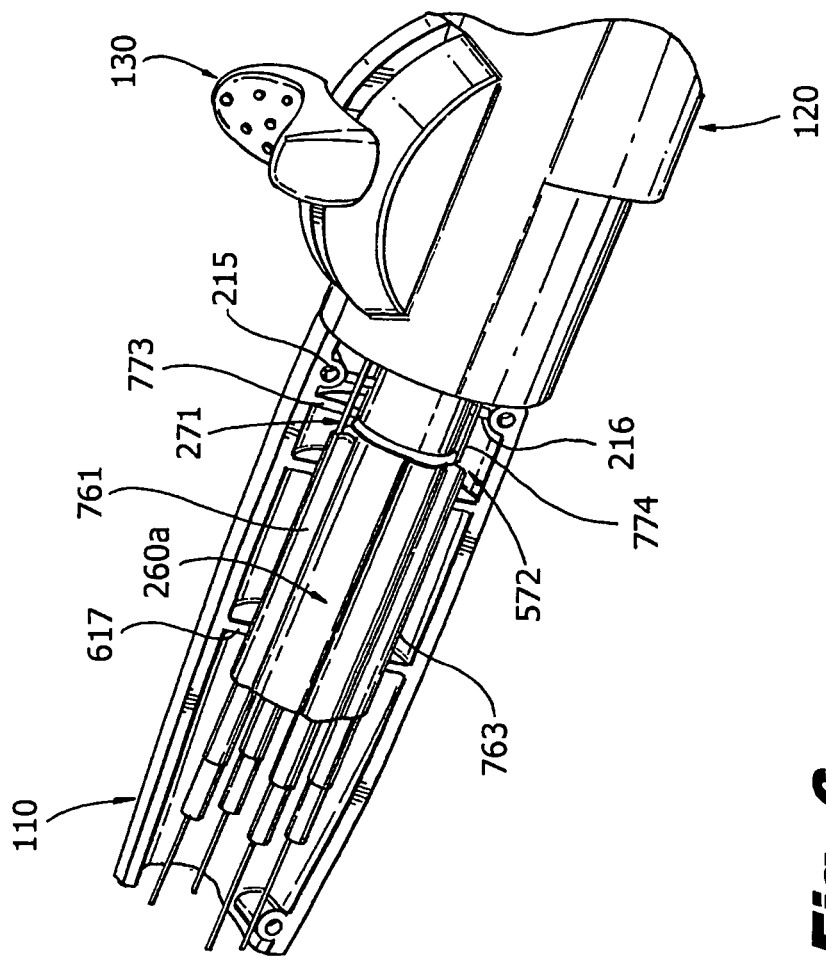
FIG. 6 is a partial cutaway view of the handle of FIG. 1.
Figure 10:
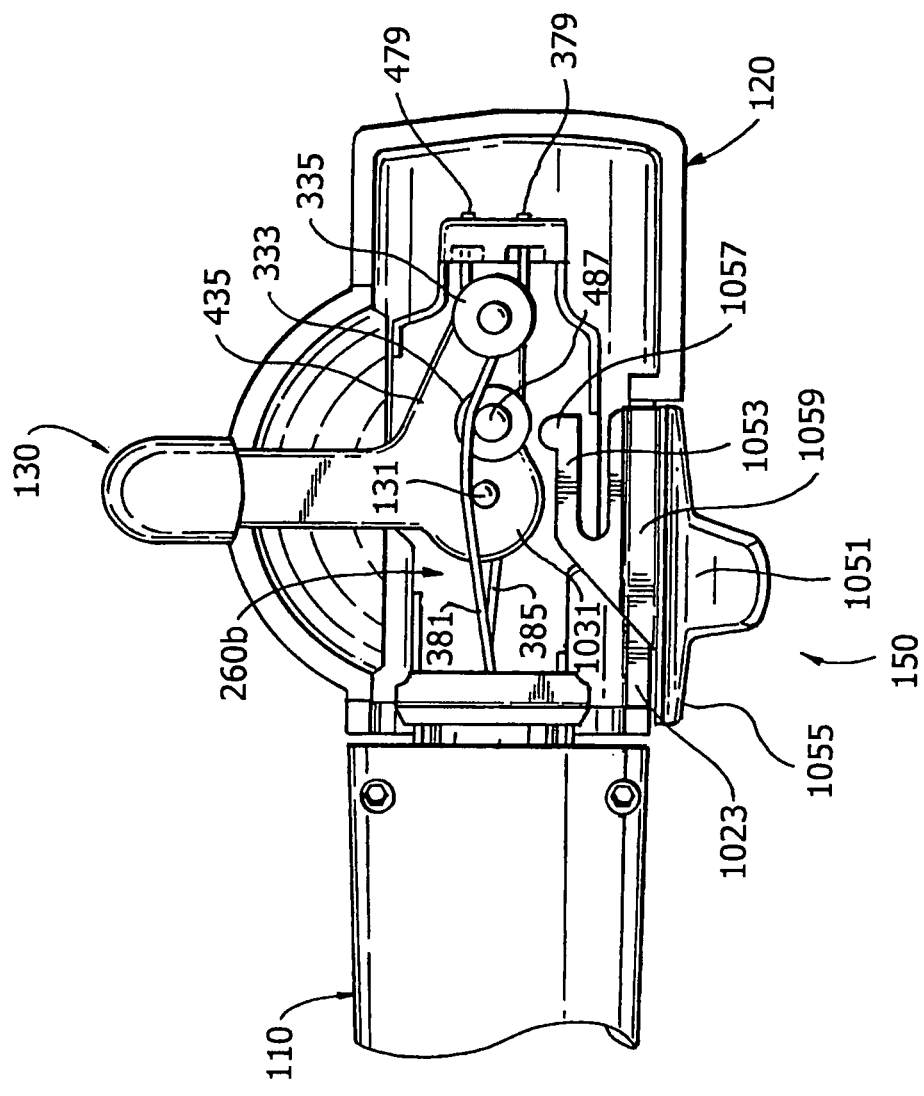
FIG. 10 is a partial cutaway view of an end of the handle of FIG. 1.

As can be seen, particularly in FIGS. 4, 5 and 10, distal movement of the lever 130 (toward a patient, for example), causes the lever 130 to rotate about pivot 131. Arm 435 of lever 130, on which a first roller 333 and second roller 335 are mounted, will move in a counter-clockwise direction about the pivot 131. Since the control cable 381 is secured at termination 379, the second roller 335 will exert decreasing tension on the control cable 381 as the lever 130 moves, until the second roller 335 is no longer in contact with the control cable 381. Thus, tension in control cable 381, and control wire 273c is minimized.

Simultaneously, during the distal motion of the lever 130, the complementary control cable 385 is placed under tension as follows. As the lever 130 and arm 435 rotate about pivot 131, a straight segment 587 of the control cable 385 is rotationally displaced from the resting position shown in FIG. 5. Since the cable 385 is secured at end termination 479, as a cable segment 589 between roller 537 and end termination 479 increases, the control cable 385 is placed in tension and the control cable 385 is drawn through the turret 260a. The spring 577 compresses due to the tension, and control wire 273d is pulled toward the operator, causing the catheter/endoscope to bend in that direction, that is, toward the right 404.

As can be seen, the control cables 381, 385 are wound around respective rollers 335, 335 and 537, 539 in opposite manners, so that motion of the lever 130 in one direction causes increased tension in one cable, while reducing tension or simply causing no tension in the complementary or opposing cable. An alternate configuration of rollers is illustrated in FIG. 11.

Figure 11:
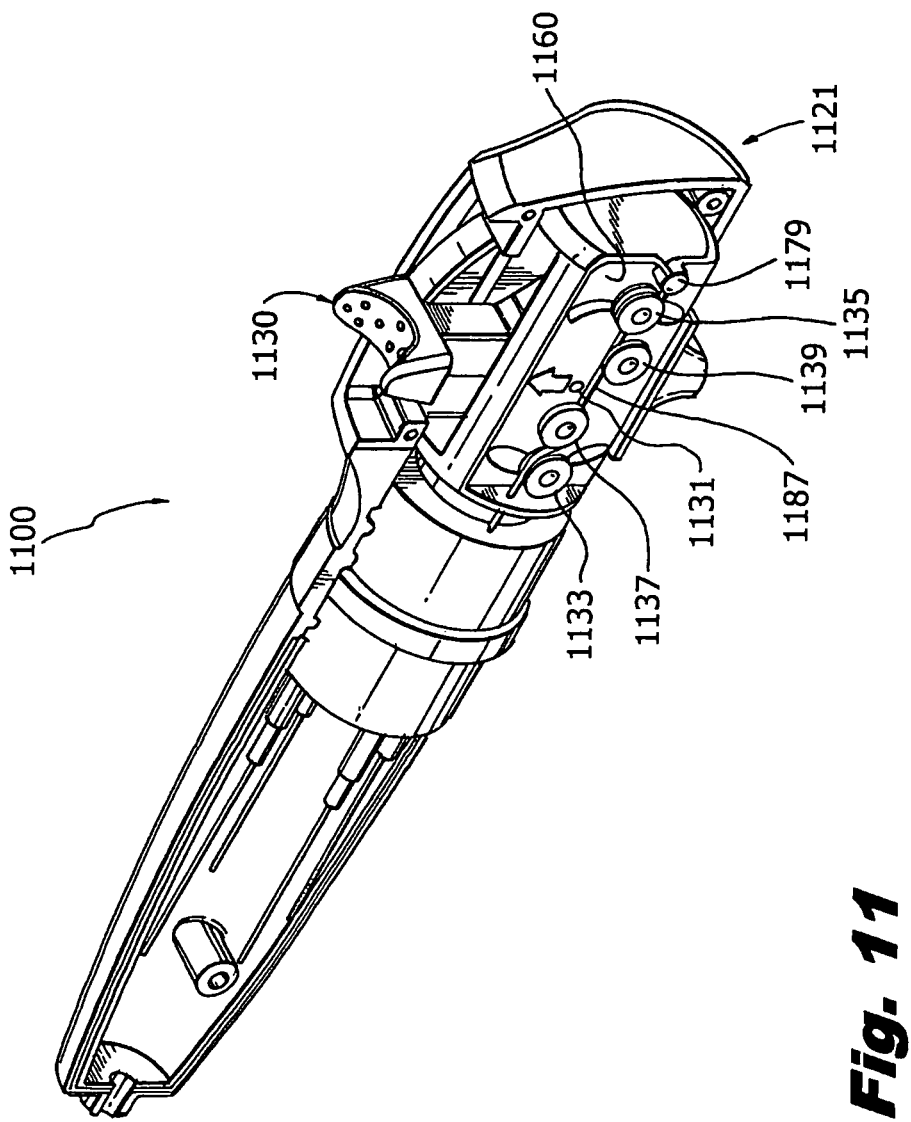
FIG. 11 is a partial cutaway isometric view of a second representative embodiment of a handle for a control mechanism for a steerable catheter or endoscope.

In FIG. 11, which illustrates an alternate embodiment of rollers to exert tension to turn the catheter/endoscope left 403 or right 404, stationary rollers 1137, 1139 are affixed to a frame 1160, while movable rollers 1133 and 1135 move in connection with motion of the lever 1130. As can be seen in FIG. 11, the control cable 1187 passes over rollers 1133 and 1139, and under rollers 1137 and 1135. Thus, when the control lever 1130, which rotates about pivot 1131, is moved proximally (toward end 1121), rollers 1133 and 1135 will displace the control cable 1187, causing tension in the control cable 1187. Since the rollers 1133 and 1135 are not directly coupled to the control cable 1187, and are only on one side thereof, respectively, distal movement of the lever 1130 will not affect the control cable 1187 on the illustrated side. However, in a similar manner to the embodiment of FIG. 1-10, the complementary control cable on the other side is oppositely wound with respect to the rollers on that side (not shown). Accordingly, distal movement of the lever 1130 causes tension in the complementary control cable while leaving the illustrated control cable 1187 unaffected.

Tension in each respective control cable will also cause a respective spring to compress. The compression of the spring will aid return of the lever 130 to a neutral position when relieved of external force by the operator.

In this manner, side-to-side motion of the catheter/endoscope can be achieved. As should be apparent to one of skill in the art, a variety of arrangements of rollers and pivot points are possible, while not departing from the scope of the present invention. Moreover, one, two, three, four or more rollers can be utilized in order to tailor the displacement of control cable to result in the desired control wire tension. Any rollers, regardless of the number of rollers, can be adjusted with respect to the pivot point of the handle, to adjust at what point, and to what extent, tension is applied or released.

Motion upward 401 and downward 402 is achieved in a slightly different manner from left 403-right 404 motion. Such upward and downward motion is achieved by exerting tension on control wires 273a and 273b through rotation of the rotatable portion 120 of the handle 100. Control cables 271 and 572 pass from respective coupling elements 270, through the turret 260a, and terminate at terminations 378 and 579, respectively at a distal wall 363 of the mechanism frame 260b.

Figure 7:
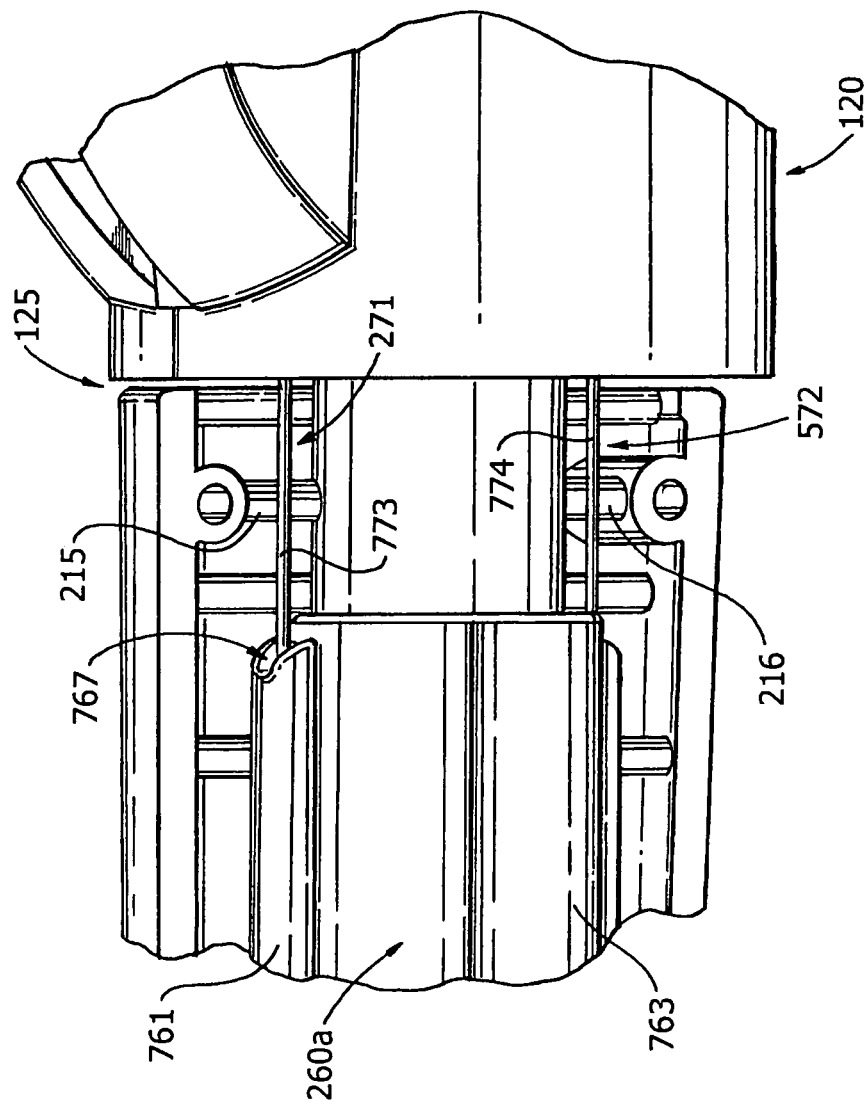
FIG. 7 is a close-up view of the view of FIG. 6.

When held by the operator, as described above, the rotatable handle portion 120 can rotate along interface 125, with respect to the main handle portion 110. The mechanism frame 260b and the turret 260a rotate in conjunction with the rotatable handle portion 120. As the rotatable handle portion 120, turret 260a and frame 260b rotate, upper and lower control cables 271, 572, which are fixed to a wall 363 of the frame 260b, either rotate freely with the turret 260a and frame 260b, or are partially restricted by one of two ribs 215, 216, depending on the direction of rotation of the rotatable handle portion 120. As can be seen in FIG. 7, an exposed portion 773, 774 of each respective control cable 271, 572 is defined between the frame 260b and lobular tubes 761, 763, respectively. The lobular tubes 761, 763 include an end (e.g., end 767) that are contoured to reduce stress concentration and/or abrasion in the control cables 271, 572 when the frame 260b and turret 260a rotate. The ribs 215, 216 are provided in the main handle portion 110 on only one side of the control cables 271, 572. Since the main handle portion 110 is composed of two halves, these ribs 215, 216 are only provided in one of the halves.

As the turret 260a and frame 260 rotate, one of the exposed control cable segments 773, 774 is prevented from rotating at a point by a respective rib 215, 216. Ends of the segments 773, 774 at the lobular tubes 761, 763 and at the terminations 378, 579 continue to rotate, thus creating tension on the respective control cable, but not on both control cables. As illustrated, for example in FIG. 6, if the rotatable handle portion 120 is rotated clockwise, with respect to the main handle portion 110, then the turret 260 will also rotate, causing the upper control cable segment 773 to deflect against the upper rib 215. This will cause increased tension in the upper control cable 271 and in the control wire 273a, causing the end of the endoscope/catheter to deflect upwardly 401. At the same time a corresponding spring in the turret 260a, if so equipped, will be compressed. With this clockwise motion, the lower control cable 572 moves away from the lower rib 216, and therefore does not experience increased tension. The compressive force experienced by the respective spring, will aide return of the rotatable handle portion 120 to a neutral position.

Similarly, if the rotatable handle portion is rotated in a counter-clockwise direction, the exposed segment 774 of the lower control cable 572 will contact the lower rib 216, deflect and cause increased tension in the lower control cable 572. This tension will result in increased tension in the lower control wire 273b. Of course, the upper control cable 271 will rotate away from the upper rib 215, and not experience increased tension. The respective return spring will be compressed and will facilitate return of the handle 120 to a neutral position.

If desired, a stop can be configured to prevent undesired excessive rotation of the rotatable handle portion 120 with respect to the main handle portion 110. If desired, additional rigidifying ribs, such as rib 617 can be provided to strengthen the main handle portion 110.

Figure 8:
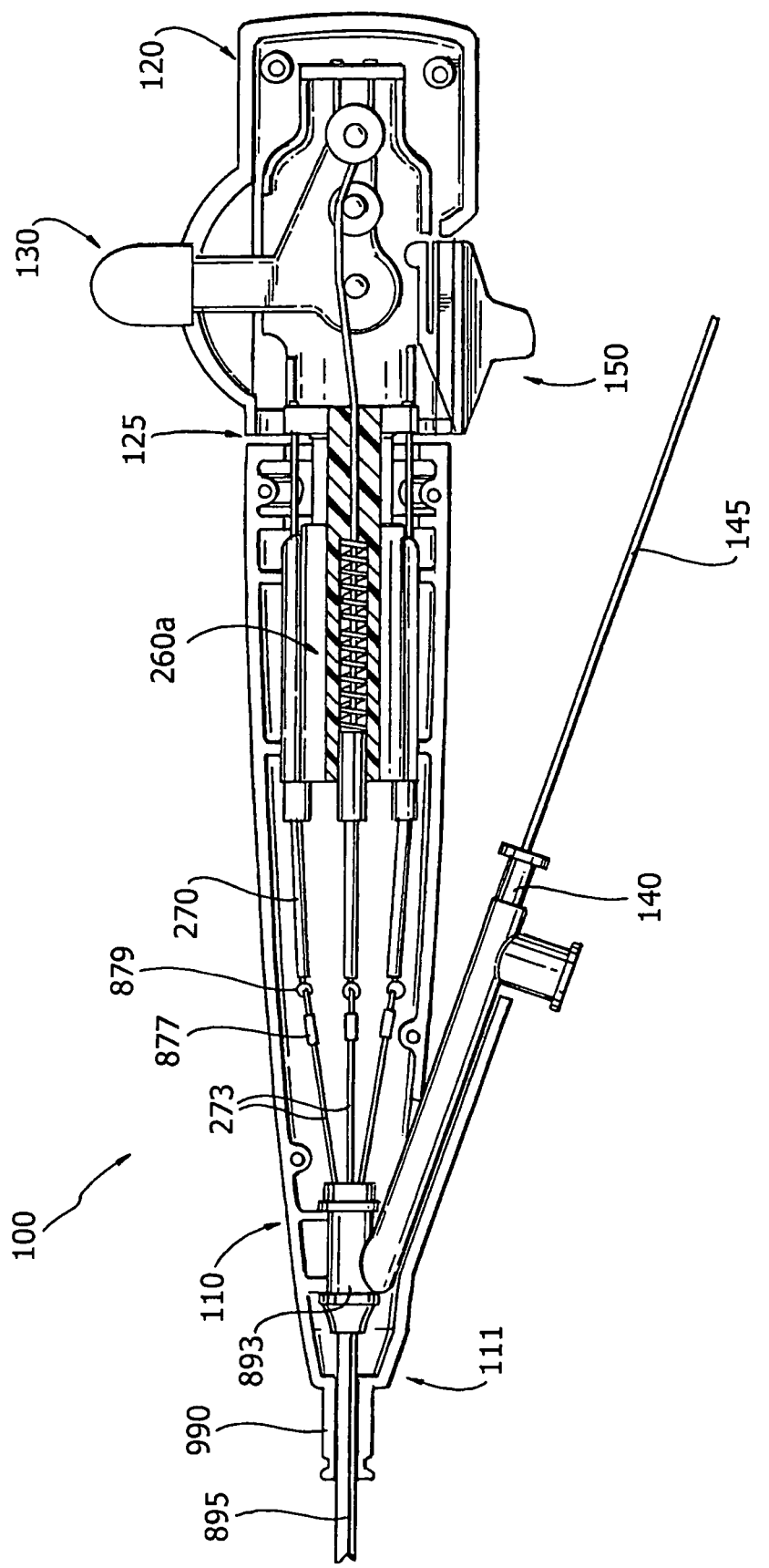
FIG. 8 is a photograph of a partial cross-sectional view of the handle of FIG. 1.
Figure 9:
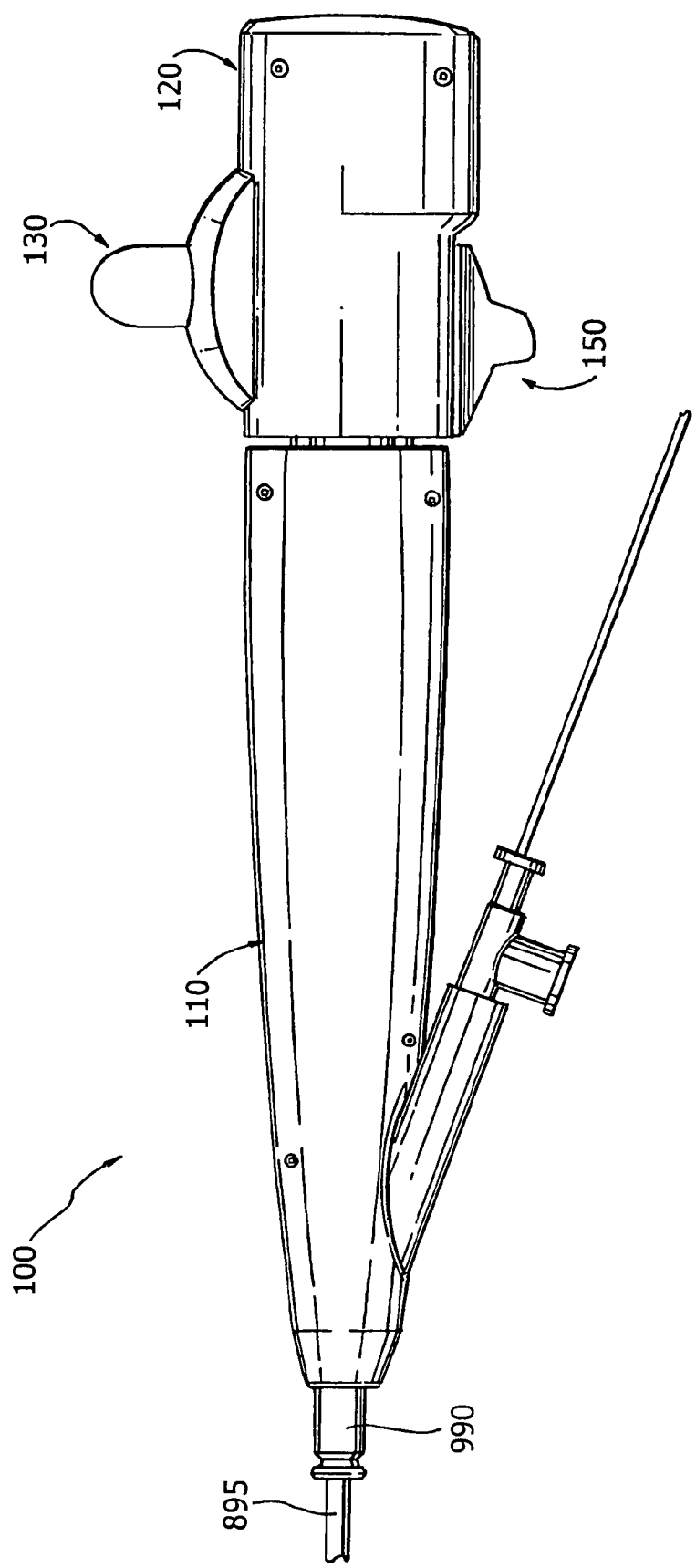
FIG. 9 is a photograph of a side view of the handle of FIG. 1.

As seen in FIGS. 8 and 9, the distal end of the handle 100 includes an adapter 893 for fitting of a catheter/endoscope tube 895, for insertion into the patient. The junction between the catheter tube 895 and the handle 100 is secured by a cover 990. Also as seen in FIG. 8, control wires (e.g. 273) can be secured to coupling elements 270 by looping the wires though an eye 879 and clamping each wire to itself with a clamp 877. Although not expressly illustrated, it is to be understood that any of the disclosed embodiments of the handle can be coupled to or formed integrally with an elongate shaft to form an entire medical device, such as a flexible or steerable endoscope or a flexible or steerable catheter.

FIG. 10 illustrates a locking mechanism 150 to lock both the displacement of the lever 130, with respect to the frame 260b, and the rotation of the rotatable handle portion 120 with respect to the main handle portion 110. The locking mechanism 150 includes a latch 1051, which includes a groove 1059 for sliding along a cutout 1023 in the wall of the rotating handle portion 120. The latch 1051 includes a pawl 1057 positioned at an end of a horizontally extending arm 1053. As the latch 1051 is moved toward the main handle portion 110, the pawl 1057 engages a lower portion 1031 of the lever 130, thereby inhibiting a change in position of the lever 130. The arm 1053 deflects and helps urge the pawl 1053 into engagement with the lower portion 1031 of the lever 130. At the same time, a distal end 1055 of the latch 1051 engages the main handle portion 110, which inhibits rotation of the rotatable handle portion 120 with respect to the main handle portion 110. The pawl 1057 can engage corresponding detents in the lever 130, or can simply engage the lever 130 by way of friction. Similarly, the distal end of the lever 1055 can engage the main handle portion 110 by way of engaging detents formed therein, or can engage the main handle portion 110 simply by way of a frictional engagement.

Materials used for the disclosed control mechanism can include any suitable material for use in a surgical environment and/or for use inside the body of a patient such as a human or other mammal. The materials used can be selected to be ones that are able to withstand typical sterilization procedures, including the use of heat, chemical sanitizers, and irradiation. In some embodiments of a control mechanism according to the invention, some or all of the elements or components of the control mechanism can be made from plastic such as acrylic, polyethylene, or the like. The control wires 273, which extend through the catheter or endoscope shaft, typically will be relatively stiff, and such control wires can be made of metal such as stainless steel. Control cables, such as cable 1187 of FIG. 11, can be made from any sufficiently strong and flexible material, and in some embodiments are made of a woven material such as a woven polypropylene rope.

The methods, systems, devices, and technology described and shown herein relate to control mechanisms that can be used with steerable or flexible medical devices such as catheters or endoscopes. Control mechanisms according to the invention allow such catheters or endoscopes to have superior properties including the practical ability to achieve 360-degree movement with the use of just a single hand of an operator (such as a surgeon or another medical professional or other person) to control the mechanism. This disclosure is not limiting, and various modifications, variations, and/or combinations can be made to what is disclosed herein and such modifications, variations, and/or combinations are considered part of this disclosure.

The invention claimed is:

1. A steering mechanism for use as part of a medical device, comprising:
 a main handle portion including a proximal end and a distal end, the main handle portion extending along a longitudinal axis, the main handle portion configured to be coupled to a medical device;
 a rotatable handle portion movably coupled to the main handle portion at an interface, the rotatable handle portion configured to be rotated about the longitudinal axis and relative to the main handle portion, the rotatable handle portion configured to move a distal end of the medical device in a first direction when rotated relative to the main handle portion; and
 a control lever axially movable along the longitudinal axis, the control lever configured to move the distal end of the medical device in a second direction different than the first direction, wherein an entirety of the control lever is disposed proximally of the interface.

2. The steering mechanism of claim 1, wherein the control lever is at least partially disposed on the rotatable handle portion.

3. The steering mechanism of claim 1, wherein the control lever is at least partially disposed on the main handle portion.

4. The steering mechanism of claim 1, wherein the rotatable handle portion and the control lever are independently movable with respect to one another.

5. The steering mechanism of claim 1, wherein the rotatable handle portion and the control lever are adapted for one-handed operation by a user.

6. The steering mechanism of claim 1, wherein the control lever is movable between a first proximal position and a second distal position, and wherein, when in the second distal position, the control lever is disposed closer to the interface than when in the first proximal position.

7. The steering mechanism of claim 1, wherein the control lever includes a plurality of gripping elements to facilitate secure control by a user's thumb.

8. The steering mechanism of claim 1, further comprising:
a plurality of control wires extending distally from the steering mechanism and terminating at one or more predetermined locations of the medical device.

9. The steering mechanism of claim 8, further comprising:
a turret coupled to the rotatable handle portion through which at least a portion of the control wires pass.

10. The steering mechanism of claim 9, wherein the turret houses a plurality of return springs.

11. The steering mechanism of claim 10, wherein the turret includes a plurality of lobular portions, at least one of the plurality of lobular portions housing at least one of the plurality of return springs.

12. The steering mechanism of claim 10, wherein each of the plurality of control wires is passed through a respective one of the plurality of return springs.

13. The steering mechanism of claim 8, further comprising:
at least one rib coupled to the main handle portion, the at least one rib configured to at least partially restrict movement of at least one of the plurality of control wires when the rotatable handle portion is rotated at least one of clockwise or counter-clockwise by a user.

14. The steering mechanism of claim 8, wherein the control lever pivots on a pin.

15. The steering mechanism of claim 8, further comprising:
a plurality of rollers between which at least a portion of the plurality of control wires pass through, the plurality of rollers configured to exert tension on at least one of the plurality control wires when the control lever is moved by a user.

16. The steering mechanism of claim 1, wherein the at least a portion of the medical device is movable in substantially any direction 360 degrees around the longitudinal axis.

17. The steering mechanism of claim 1, further comprising:
a locking mechanism to prevent rotation of the rotatable handle portion with respect to the main handle portion.

18. The steering mechanism of claim 1, further comprising:
a locking mechanism to prevent movement of the control lever with respect to the main handle portion.

19. A steering mechanism for use as part of a medical device, comprising:
a main handle portion including a proximal end and a distal end, the main handle portion extending along a longitudinal axis, the main handle portion configured to be coupled to a medical device;
a rotatable handle portion movably coupled to the main handle portion at an interface, the rotatable handle portion including a proximal end and a distal end, the distal end of the rotatable handle portion disposed adjacent the proximal end of the main handle portion, the rotatable handle portion configured to be rotated about a first axis, the first axis being substantially parallel to the longitudinal axis, the rotatable handle portion configured such that rotation of the rotatable handle portion with respect to the main handle portion causes a distal end of the medical device to move in a first direction; and
a control lever movable about a second axis substantially perpendicular to the first axis, an entirety of the control lever being disposed proximally of the interface, wherein the control lever is configured to move the distal end of the medical device in a second direction different from the first direction, the control lever is movable between a first proximal position and a second distal position, and, when in the second distal position, the control lever is positioned closer to the interface than when in the first proximal position.

20. The steering mechanism of claim 19, further comprising;
a turret coupled to the rotatable handle portion through which at least one of a plurality of control wires pass, the plurality of control wires extending distally from the steering mechanism and terminating at one or more predetermined locations of the steerable medical device, the turret coupled to the rotatable handle portion such that the turret is rotated about the first axis corresponding to rotation of the rotatable handle portion about the first axis.

21. The steering mechanism of claim 20, wherein the turret houses a plurality of return springs.

22. The steering mechanism of claim 21, wherein at least one of the plurality of control wires is passed through at least one of the plurality of return springs.

23. The steering mechanism of claim 19, wherein the turret includes a plurality of lobular portions, the lobular portions housing a plurality of return springs.

24. The steering mechanism of claim 19, further comprising:
a plurality of rollers between which pass at least a portion of the plurality of control wires, at least one roller of the plurality of rollers configured to exert tension on at least one of the plurality of control wires when the control lever is moved about the second axis.

25. The steering mechanism of claim 19, further comprising:
a locking mechanism movably coupled to the rotatable handle portion and engageable with each of the main handle portion and the control lever, the locking mechanism configured to prevent rotation of the rotatable handle portion with respect to the main handle portion, the locking mechanism configured to prevent movement of the control lever about the second axis.

26. The steering mechanism of claim 19, wherein the rotatable handle portion includes a frame rigidly coupled to a turret through which at least one of a plurality of control wires pass, the plurality of control wires extending distally from the steering mechanism and terminating at one or more predetermined locations of the steerable medical device, a portion of the control lever being received by the frame.

* * * * *